US007008631B2

(12) United States Patent
Ashley

(10) Patent No.: US 7,008,631 B2
(45) Date of Patent: Mar. 7, 2006

(54) METHODS OF SIMULTANEOUSLY TREATING OCULAR ROSACEA AND ACNE ROSACEA

(75) Inventor: Robert A. Ashley, Newtown, PA (US)

(73) Assignee: CollaGenex Pharmaceuticals, Inc., Newton, PA (US)

(*) Notice: Subject to any disclaimer, the term of this patent is extended or adjusted under 35 U.S.C. 154(b) by 0 days.

(21) Appl. No.: 10/414,808

(22) Filed: Apr. 16, 2003

(65) Prior Publication Data

US 2003/0229055 A1 Dec. 11, 2003

Related U.S. Application Data

(60) Provisional application No. 60/373,141, filed on Apr. 16, 2002.

(51) Int. Cl.
*A61K 6/00* (2006.01)
*A61K 9/20* (2006.01)
*A61K 31/65* (2006.01)

(52) U.S. Cl. .................. 424/401; 424/464; 514/152
(58) Field of Classification Search ............ 424/464, 424/401, 449
See application file for complete search history.

(56) References Cited

U.S. PATENT DOCUMENTS

| | | | |
|---|---|---|---|
| 4,957,918 A * | 9/1990 | Martin et al. ............ 514/235.8 |
| 5,908,838 A | 6/1999 | Gans | |
| 6,015,803 A | 1/2000 | Wirostko | |
| 6,296,880 B1 * | 10/2001 | Murad ...................... 424/616 |
| 6,384,081 B1 | 5/2002 | Berman | |
| 6,455,583 B1 | 9/2002 | Pflugfelder et al. | |
| 6,495,158 B1 * | 12/2002 | Buseman et al. ............ 424/443 |
| 6,664,287 B1 * | 12/2003 | Avery et al. ................ 514/436 |
| 2004/0092491 A1 | 5/2004 | Nieman et al. ............. 514/152 |

FOREIGN PATENT DOCUMENTS

| | | |
|---|---|---|
| WO | 99/58131 | 11/1999 |
| WO | WO 9958131 A1 * | 11/1999 |
| WO | 00/07601 | 2/2000 |

OTHER PUBLICATIONS

Bikowski JB "Treatment of rosacea with doxycycline monohydrate", Cutis, Aug. 2000, 66(2): 149-52.*
Nazir et al. "Ocular rosacea in childhood", Am J Ophthalmol, Jan. 2004: 137(1):138-44.*
Quarterman et al. "Ocular rosacea. Signs, symptoms, and tear studies before and after treatment with doxycycline" Arch Dermatol, Jan. 1997; 133(1):49-54.*
Freinkel et al. "Effect of tetracycline on the composition of sebum in acne vulgaris." *New England Journal of Medicine*, 1965, vol. 273, No. 16, pp. 850-854, (abstract only).
Dursun D. et al. "Treatment of recalcitrant recurrent corneal erosions with inhibitors of matrix metalloproteinase-9, doxycycline and corticosteroids." *Am. J. Ophthalmol.*, 132 (1):8-13 (Jul. 2001).
Dursun D. et al. "Pseudokeratoconus caused by rosacea." *Cornea*, 20(6):668-9 (Aug. 2001).

(Continued)

*Primary Examiner*—Thurman K. Page
*Assistant Examiner*—S. Tran
(74) *Attorney, Agent, or Firm*—Hoffmann & Baron, LLP

(57) ABSTRACT

A method for simultaneously treating ocular rosacea and acne rosacea in a human in need thereof comprising administering systemically to said human a tetracycline compound in an amount that is effective to treat ocular rosacea and acne rosacea but has substantially no antibiotic activity.

3 Claims, 2 Drawing Sheets

Sample Dose Response Showing the Positive Control Chlorpromazine

OTHER PUBLICATIONS

Li DQ, et al. "Regulation of MMP-9 production by human corneal epithelial cells." *Exp. Eye Res.*, 73(4):449-59 (Oct. 2001).

Solomon A., et al. "Doxycycline inhibition of interleukin-1 in the corneal epithelium." *Invest. Ophthalmol Vis. Sci.*, 41(9):2544-57 (Aug. 2000).

Sobrin L., et al. "Regulation of MMP-9 activity in human tear fluid and corneal epithelial culture supernatant." *Invest. Ophthalmol. Vis. Sci.*, 41(7):1703-9 (Jun. 2000).

Gilbard JP., et al. "Dry eye, blepharitis and chronic eye irritation: divide and conquer." *J. Ophthalmic Nurs. Technology*, 18(3): 109-15 (May-Jun. 1999).

Bikowksi, J.B., "Treatment of rosacea with doxycycline monohydrate," Curtis. Aug. 2000, 66(2):149-152.

Jimenez-Acosta, "Response to tetracycline of telanglectasias in male hemophiliac with human immunodeficiency virus infection," J. Am. Acad. Dermatol. Aug. 1988, 19(2 Pt. 1):369-379.

Torresani, C., "Clarithromycin versus doxycycline in the treatment of rosacea," Int. J. Clin. Dermatol Dec. 1997, 36(12):942-946.

McClellan, K.J., "Topical Metronidazole. A review of its use in rosaea," Am. J. Clin. Dermatol. May-Jun. 2000, 1(3):191-199.

Quarterman, M.J., "Ocular Rosacea. Signs, symptoms and tear studies before and after treatment with doxycycline," Arch. Dermatol. Jan. 1997, 133(1):49-54.

* cited by examiner

FIG. 1 PHOTOTOXICITY INDEX

Sample Dose Response Showing the Positive Control Chlorpromazine

□ % Viability (+UV)
◇ % Viability (-UV)

METHODS OF SIMULTANEOUSLY TREATING OCULAR ROSACEA AND ACNE ROSACEA

The present application claims benefit of U.S. provisional application Ser. No. 60/373,141, filed Apr. 16, 2002, which is incorporated herein by reference.

BACKGROUND OF THE INVENTION

Ocular rosacea is a common tear film and ocular surface disorder causing eye irritation. This disorder is characterized by eye surface inflammation, and a variety of related eye disorders such as blepharitis; meibomian gland disease, including meibomian gland dysfunction and meibomianitis; keratitis; conjunctival hyperemia; and eyelid hyperemia.

A conservative estimate of the number of patients affected with ocular rosacea is 10 million in the United States alone. It has been reported that 15% of patients with ocular rosacea develop recurrent corneal epithelial erosions, a potentially sight-threatening problem. The incidence of ocular rosacea increases with age.

Common complaints of patients suffering from ocular rosacea include blurred or filmy vision, burning or foreign body sensations in the eye, photophobia, and pain severe enough to awaken the person from sleep. Anterior erosion of the mucocutaneous junction of the eyelid is often noted, as well as eyelid and conjunctival infection, eyelid margin irregularity, corneal epithelial changes, and corneal vascularization.

Although patients with ocular rosacea usually have a normal production of aqueous tears by their lacrimal glands, their meibomian glands can atrophy. The meibomian glands are situated upon the inner surface of the eyelids, between the tarsal plates and conjunctiva. The oily secretions of these glands lubricate the eyelids.

Ocular rosacea is characterized by inflammation of the eyelids, referred to as blepharitis. Blepharitis can be categorized anatomically into anterior and posterior blepharitis.

Anterior blepharitis refers to inflammation mainly centered around the eyelashes and follicles. Anterior blepharitis usually is subdivided further into staphylococcal and seborrheic variants. Frequently, a considerable overlap exists in these processes in individual patients.

Posterior blepharitis mainly is related to dysfunction of the meibomian glands. Alterations in secretory metabolism and function lead to disease. The meibomian secretions become more waxlike and begin to block the gland orifices. The stagnant material becomes a growth medium for bacteria and can seep into the deeper eyelid tissue layers, causing inflammation. These processes lead to gland plugging, inspissated material, formation of chalazia and meibomianitis.

Meibomianitis is characterized by inflammation centered about the meibomian glands. The inflammation can lead to meibomian gland dysfunction, which is characterized by the loss of meibomian gland oil from the tear film, an increase in tear film evaporation, a loss of water from the tear film and the development of dry eye surface disease.

Methods of treating ocular rosacea have included treatment of the apparent infection/inflammation of the eyelids or meibomian glands. For example, patients with ocular rosacea have been symptomatically treated with artificial tears, or hot compresses which liquefy the secretions of the meibomian glands. However, these methods provide limited, if any, improvement. Also, patients have been treated with topically applied steroids to the eyelids or ocular surface. However, steroids are not good long-term solutions because of the potential side-effects e.g., cataract and glaucoma.

Additionally, orally administered tetracyclines and tetracycline analogues (e.g., doxycycline and minocycline) having antibiotic activity are commonly and effectively used for prophylactic or therapeutic treatment of meibomian gland disease. However, a disadvantage of using systemically administered antibiotic tetracyclines is that a high percentage of patients are unable to tolerate oral tetracyclines for extended periods of time. Also, patients can build up a resistance to antibiotic tetracyclines.

Recently other methods for treating ocular rosacea have been disclosed. For example, Gilbard discloses topical antibiotic tetracyclines for the treatment of ocular rosacea (International Application WO 00/07601). Additionally, Pflugfelder et al. have disclosed the use of systemic and topical tetracyclines at a sub-antimicrobial dose for the treatment of ocular rosacea (International Application WO 99/58131).

The skin disease acne rosacea often accompanies ocular rosacea. In particular, ocular rosacea is present in approximately 60% of individuals with acne rosacea.

Acne rosacea is characterized by inflammatory lesions and permanent dilation of blood vessels. Acne rosacea can also include papules, pustules, and hypertrophic sebaceous glands in facial flush areas. A manifestation of severe acne rosacea is rhinophyma. Rhinophyma is seen more often in men with acne rosacea than in women. Rhinophyma is characterized by a thickened, lobulated overgrowth of the sebaceous glands and epithelial connective tissue of the nose.

It is well known that acne and ocular rosacea commonly occur together. Nevertheless, no one has disclosed the simultaneous treatment of both disorders.

Since many patients are susceptible to the simultaneous occurrence of both acne rosacea and ocular rosacea, there is a need for a method of simultaneously treating a patient suffering from both types of disorders. It is especially advantageous if a single agent would be effective to treat both types of disorders. The use of a single agent would reduce both the cost and risk of side effects of treatment.

SUMMARY OF INVENTION

The present invention provides a method for simultaneously treating ocular rosacea and acne rosacea in a human in need thereof. The method comprises administering systemically to the human a tetracycline compound in an amount that is effective to treat ocular rosacea and acne rosacea but has substantially no antibiotic activity.

| COL | R7 | R8 | R9 |
|-----|----|----|----|
| 308 | hydrogen | hydrogen | amino |
| 311 | hydrogen | hydrogen | palmitamide |
| 306 | hydrogen | hydrogen | dimethylamino |

For structures L, M, N or O the compounds indicated are as follows:

| COL | R7 | R8 | R9 |
|---|---|---|---|
| 801 | hydrogen | hydrogen | acetamido |
| 802 | hydrogen | hydrogen | dimethylaminoacetamido |
| 804 | hydrogen | hydrogen | nitro |
| 805 | hydrogen | hydrogen | amino |

For structure P, R8 is hydrogen and R9 is nitro (COL-1002).

Figure 1:
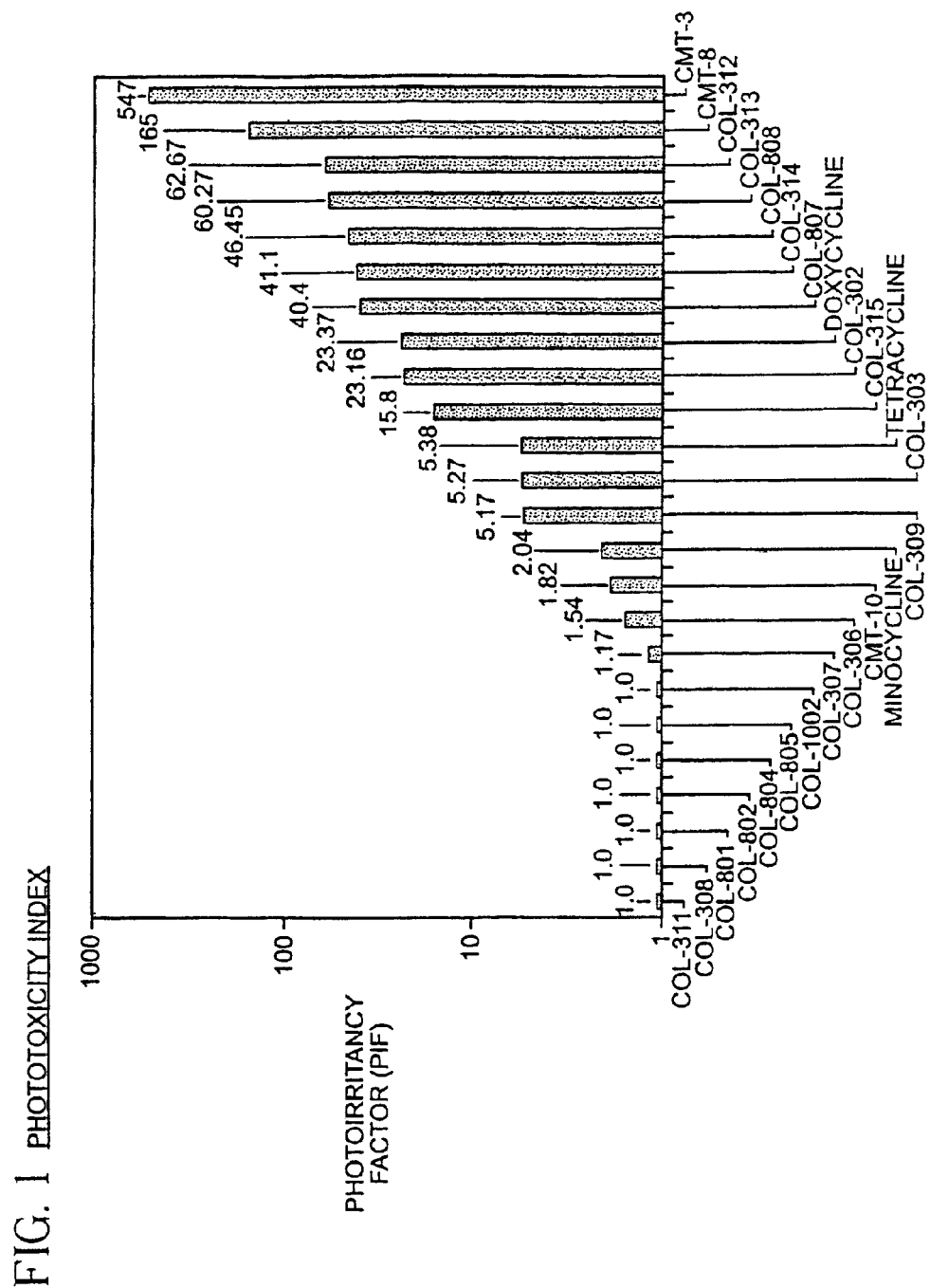
FIG. 1 shows the photoirritancy factor (PIF) for some tetracycline compounds. For structure K, the compounds indicated are as follows.
Figure 2:
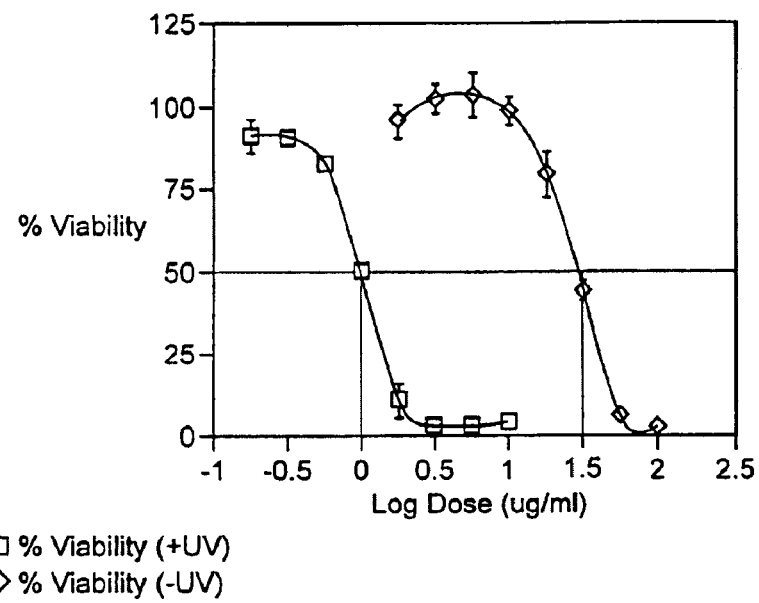

FIG. 2 shows a Sample Dose Response Curve of the Positive Control Chlorpromazine for use in PIF calculations.

Figure 3:
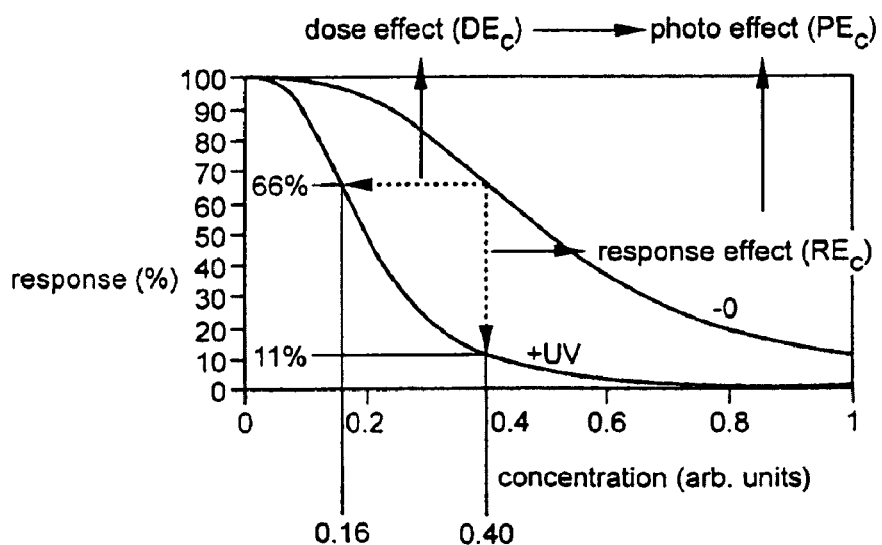

FIG. 3 shows a Sample Dose Response Curve for use in MPE calculations.

DETAILED DESCRIPTION

The present invention provides a method for simultaneously treating ocular rosacea and acne rosacea.

As used herein, the term "ocular rosacea" is a disorder characterized by eye surface inflammation, and a variety of related eye disorders such as blepharitis; meibomian gland disease, including meibomianitis; keratitis; conjunctival hyperemia; and eyelid hyperemia. The eye surface includes the eyelids, cornea and conjunctiva.

The present invention is particularly effective in treating all known types of blepharitis. Some types of blepharitis include, for example, blepharitis angularis, blepharitis ciliaris, blepharitis marginalis, nonulcerative blepharitis, seborrheic blepharitis, blepharitis squamosa, squamous seborrheic blepharitis, and blepharitis ulcerosa.

Acne rosacea is a skin condition characterized by inflammatory lesions (erythema) and permanent dilation of blood vessels (telangectasia). Acne rosacea can also include papules, pustules, and hypertrophic sebaceous glands in facial flush areas. A manifestation of severe acne rosacea is rhinophyma. Rhinophyma is characterized by a thickened, lobulated overgrowth of the sebaceous glands and epithelial connective tissue of the nose.

The method of the present invention comprises the administration of a tetracycline compound to a human in an amount which is effective for its purpose e.g., the simultaneous treatment of ocular rosacea and acne rosacea, but which has substantially no antibiotic activity. Preferably, the human is monitored. Monitoring is accomplished by observing a positive result. A positive result includes reducing or reversing the symptoms characterizing ocular rosacea and acne rosacea.

The tetracycline compound can be an antibiotic or non-antibiotic compound. The tetracyclines are a class of compounds of which tetracycline is the parent compound. Tetracycline has the following general structure:

Structure A

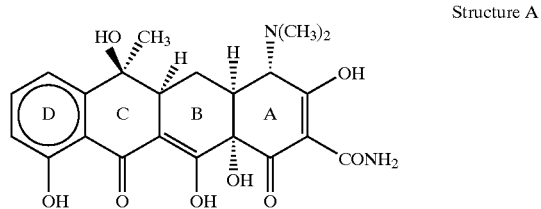

The numbering system of the multiple ring nucleus is as follows:

Structure B

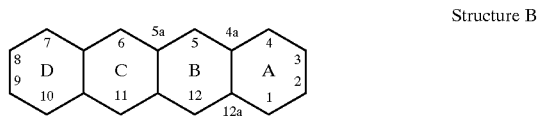

Tetracycline, as well as the 5-hydroxy (oxytetracycline, e.g. Terramycin) and 7-chloro (chlorotetracycline, e.g. Aureomycin) derivatives, exist in nature, and are all well known antibiotics. Semisynthetic derivatives such as 7-dimethylaminotetracycline (minocycline) and 6α-deoxy-5-hydroxytetracycline (doxycycline) are also known tetracycline antibiotics. Natural tetracyclines may be modified without losing their antibiotic properties, although certain elements of the structure must be retained to do so.

Some examples of antibiotic (i.e. antimicrobial) tetracycline compounds include doxycycline, minocycline, tetracycline, oxytetracycline, chlortetracycline, demeclocycline, lymecycline and their pharmaceutically acceptable salts. Doxycycline is preferably administered as its hyclate salt or as a hydrate, preferably monohydrate.

Non-antibiotic tetracycline compounds are structurally related to the antibiotic tetracyclines, but have had their antibiotic activity substantially or completely eliminated by chemical modification. For example, non-antibiotic tetracycline compounds are capable of achieving antibiotic activity comparable to that of tetracycline or doxycycline at concentrations at least about ten times, preferably at least about twenty five times, greater than that of tetracycline or doxycycline, respectively.

Examples of chemically modified non-antibiotic tetracyclines (CMTs) include 4-de(dimethylamino)tetracycline (CMT-1), tetracyclinonitrile (CMT-2), 6-demethyl-6-deoxy-4-de(dimethylamino)tetracycline (CMT-3), 7-chloro-4-de(dimethylamino)tetracycline (CMT-4), tetracycline pyrazole (CMT-5), 4-hydroxy-4-de(dimethylamino)tetracycline (CMT-6), 4-de(dimethylamino)-12α-deoxytetracycline (CMT-7), 6-deoxy-5α-hydroxy-4-de(dimethylamino)tetracycline (CMT-8), 4-de(dimethylamino)-12α-deoxyanhydrotetracycline (CMT-9), 4-de(dimethylamino)minocycline (CMT-10). (COL and CMT are used interchangeably throughout this specification.)

Further examples of chemically modified non-antibiotic tetracyclines include Structures C–Z. (See Index of Structures.)

Tetracycline derivatives, for purposes of the invention, may be any tetracycline derivative, including those compounds disclosed generically or specifically in co-pending U.S. patent application Ser. No. 09/573,654, filed on May 18, 2000; and Ser. No. 10/274,841, filed on Oct. 18, 2002, which are incorporated herein by reference.

The tetracycline compound is administered in an amount which is effective to simultaneously treat ocular rosacea and acne rosacea, but which has substantially no antibiotic effect. A treatment is effective if it causes a reduction or inhibition of the symptoms associated with ocular rosacea and acne rosacea.

The minimal effective amount of a tetracycline compound administered to a human is the lowest amount capable of providing effective simultaneous treatment of ocular rosacea and acne rosacea. Some examples of minimal amounts include 10%, 20%, 30% and 40% of an antibiotic amount.

The maximal effective amount of a tetracycline compound administered to a human is the highest amount that does not significantly prevent the growth of microbes, e.g., bacteria. Some examples of maximal amounts include 50%, 60%, 70% and 80% of an antibiotic amount.

The amount of a tetracycline compound which is administered can be measured by daily dose and by serum level.

Tetracycline compounds that have significant antibiotic activity may, for example, be administered in a dose which is 10–80% of the antibiotic dose. More preferably, the antibiotic tetracycline compound is administered in a dose which is 40–70% of the antibiotic dose.

Antibiotic daily doses are known in art. Some examples of antibiotic doses of members of the tetracycline family include 50, 75, and 100 mg/day of doxycycline; 50, 75, 100, and 200 mg/day of minocycline; 250 mg of tetracycline one, two, three, or four times a day; 1000 mg/day of oxytetracycline; 600 mg/day of demeclocycline; and 600 mg/day of lymecycline.

Examples of the maximum non-antibiotic doses of tetracyclines based on steady-state pharmacokinetics are as follows: 20 mg/twice a day for doxycycline; 38 mg of minocycline one, two, three or four times a day; and 60 mg of tetracycline one, two, three or four times a day.

In a preferred embodiment, doxycycline is administered in a daily amount of from about 30 to about 60 milligrams, but maintains a concentration in human plasma below the threshold for a significant antibiotic effect.

In an especially preferred embodiment, doxycycline hyclate is administered at a 20 milligram dose twice daily. Such a formulation is sold for the treatment of periodontal disease by CollaGenex Pharmaceuticals, Inc. of Newtown, Pa. under the trademark Periostat®.

The administered amount of a tetracycline compound described by serum levels follows.

An antibiotic tetracycline compound is advantageously administered in an amount that results in a serum tetracycline concentration which is 10–80%, preferably 40–70%, of the minimum antibiotic serum concentration. The minimum antibiotic serum concentration is the lowest concentration known to exert a significant antibiotic effect.

Some examples of the approximate antibiotic serum concentrations of members of the tetracycline family follow. A single dose of two 100 mg minocycline HCl tablets administered to adult humans results in minocycline serum levels ranging from 0.74 to 4.45 $\mu$g/ml over a period of an hour. The average level is 2.24 $\mu$g/ml.

Two hundred and fifty milligrams of tetracycline HCl administered every six hours over a twenty-four hour period produces a peak plasma concentration of approximately 3 $\mu$g/ml. Five hundred milligrams of tetracycline HCl administered every six hours over a twenty-four hour period produces a serum concentration level of 4 to 5 $\mu$g/ml.

In one embodiment, the tetracycline compound can be administered in an amount which results in a serum concentration between about 0.1 and 10.0 $\mu$g/ml, more preferably between 0.3 and 5.0 $\mu$g/ml. For example, doxycycline is administered in an amount which results in a serum concentration between about 0.1 and 0.8 $\mu$g/ml, more preferably between 0.4 and 0.7 $\mu$g/ml.

Some examples of the plasma antibiotic threshold levels of tetracyclines based on steady-state pharmacokinetics are as follows: 1.0 $\mu$g/ml for doxycycline; 0.8 $\mu$g/ml for minocycline; and 0.5 $\mu$g/ml for tetracycline.

Non-antibiotic tetracycline compounds can be used in higher amounts than antibiotic tetracyclines, while avoiding the indiscriminate killing of microbes, and the emergence of resistant microbes. For example, 6-demethyl-6-deoxy-4-de(dimethylamino)tetracycline (CMT-3) may be administered in doses of about 40 to about 200 mg/day, or in amounts that result in serum levels of about 1.55 $\mu$g/ml to about 10 $\mu$g/ml.

The actual preferred amounts of tetracycline compounds in a specified case will vary according to the particular compositions formulated, the mode of application, the particular sites of application, and the subject being treated (e.g. age, gender, size, tolerance to drug, etc.)

The tetracycline compounds can be in the form of pharmaceutically acceptable salts of the compounds. The term "pharmaceutically acceptable salt" refers to a salt prepared from tetracycline compounds and pharmaceutically acceptable non-toxic acids or bases. The acids may be inorganic or organic acids of tetracycline compounds. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylenediamine, chloroprocaine, choline, diethanolamine, ethylenediamine, meglumine (N-methylglucamine), and procaine.

The tetracycline compounds mentioned above, especially doxycycline and minocycline, are unexpectedly effective in reducing the number of comedones when administered at a dose which has substantially no antibiotic effect. Preferably the reduction is at least about 20% greater than for a placebo control, more preferably at least about 30% greater than for a placebo control, most preferably at least about 40% greater than for a placebo control, and optimally at least about 50% greater than for a placebo control.

Preferably, the tetracycline compounds have low phototoxicity, or are administered in an amount that results in a serum level at which the phototoxicity is acceptable. Phototoxicity is a chemically-induced photosensitivity. Such photosensitivity renders skin susceptible to damage, e.g. sunburn, blisters, accelerated aging, erythemas and eczematoid lesions, upon exposure to light, in particular ultraviolet light. The preferred amount of the tetracycline compound produces no more phototoxicity than is produced by the administration of a 40 mg total daily dose of doxycycline.

There are several methods by which to quantify phototoxicity. One method is called photoirritancy factor (PIF). The PIF is the ratio of an $IC_{50}$ value in the absence of light to an $IC_{50}$ value in the presence of light.

In calculating PIF values, the data resulting from the assay procedure can be interpreted by different methods. For example, during the period Mar. 2, 1999 to Apr. 16, 1999, PIF values were obtained using the phototoxicity software and its curve-fitting algorithms available at the time. In the present specification, this earlier phototoxicity calculation is referred to as PIF1. At a PIF1 value of 1, a compound is considered to have no measurable phototoxicity. A PIF1 value greater than 5 is indicative of phototoxic potential of a compound.

As explained in more detail in Example 37 below, 3T3 phototoxicity assay has undergone extensive validation since April 1999, and has now been incorporated into a draft guideline by the Organization of Economic Cooperation and Development (OECD) (Draft Guideline 432). In the present specification, this revised phototoxicity calculation is referred to as PIF2. A PIF2 value of less than 2 is considered non-phototoxic, 2 to less than 5 is considered potentially phototoxic, and 5 or greater is considered clearly phototoxic.

PIF2 values are more refined than the PIF1 values. Qualitatively the differences between the PIF1 and PIF2 values are not significant. For example, the mean PIF1 values for COL 10 and COL 1002 are 1.82 and 1.0, respectively. The mean PIF2 values of COL 10 and COL 1002 are 2.04 and 1.35, respectively.

As explained in the Examples section, PIF values cannot be determined for many compounds. Another method by which to quantify relative phototoxicity is called mean photo effect (MPE). MPE values can be determined for compounds in virtually all cases. Thus, MPE values are more consistent and reliable than PFE values.

The MPE is a measure of the difference between the cytotoxicity induced by the test chemical in the presence and absence of light. It compares the responses over the range of doses selected using the two dose-response curves produced from the boot-strap analysis of the individual data points (Holzhütter 1995 and 1997). An example is provided in FIG. 3 (Peters and Holzhütter (2002)). This method of analysis is particularly suited to cases where the $IC_{50}$ value cannot be calculated for one or both concentration response curves.

MPE values of <0.1 (including negative values) are considered indicative of a nonphototoxin, values of 0.1 to <0.15 are considered probable phototoxins, and values greater than and equal to 0.15 are considered to be clear phototoxins.

A class of low phototoxicity tetracyline derivatives has less than approximately 75% of the phototoxicity of minocycline, preferably less than approximately 70%, more preferably less than approximately 60%, and most preferably less than approximately 50%. Minocycline has a PIF1 of about 2.04, and an MPE of about 0.041.

The class of low phototoxicity tetracycline compound derivatives includes those derivatives having PIF1 or PIF2 values of approximately 1, i.e. 1 to about 2, preferably 1 to about 1.5. The class of low phototoxicity tetracycline derivatives optimally have MPE values of less than 0.1. Members of this class include, but are not limited to, tetracycline compounds having general formulae:

Structure K wherein: R7, R8, and R9 taken together in each case, have the following meanings:

| R7 | R8 | R9 |
|---|---|---|
| hydrogen | hydrogen | amino |
| hydrogen | hydrogen | palmitamide |
| hydrogen | hydrogen | dimethylamino |
| trimethylammonium | hydrogen | hydrogen |
| and | | |
| STRUCTURE L | | STRUCTURE M |
| STRUCTURE N | | STRUCTURE O | wherein: R7, R8, and R9 taken together in each case, have the following meanings:

| R7 | R8 | R9 |
|---|---|---|
| hydrogen | hydrogen | acetamido |
| hydrogen | hydrogen | dimethylaminoacetamido |
| hydrogen | hydrogen | nitro |
| hydrogen | hydrogen | amino |
| | and | |
| | STRUCTURE P | | wherein: R8, and R9 taken together are, respectively, hydrogen and nitro.

The tetracycline compounds may, for example, be administered systemically. For the purposes of this specification, "systemic administration" means administration to a human by a method that causes the compounds to be absorbed into the bloodstream.

For example, the tetracyclines compounds can be administered orally by any method known in the art. For example, oral administration can be by tablets, capsules, pills, troches, elixirs, suspensions, syrups, wafers, chewing gum and the like.

Additionally, the tetracycline compounds can be administered enterally or parenterally, e.g., intravenously; intramuscularly; subcutaneously, as injectable solutions or suspensions; intraperitoneally; or rectally. Administration can also be intranasally, in the form of, for example, an intranasal spray; or transdermally, in the form of, for example, a patch.

For the pharmaceutical purposes described above, the tetracycline compounds of the invention can be formulated per se in pharmaceutical preparations optionally with a suitable pharmaceutical carrier (vehicle) or excipient as understood by practitioners in the art. These preparations can be made according to conventional chemical methods.

In the case of tablets for oral use, carriers which are commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the tetracycline compounds can be employed, and the pH of the solutions can be suitably adjusted and buffered. For intravenous use, the total concentration of the solute(s) can be controlled in order to render the preparation isotonic.

The tetracycline compounds of the present invention can further comprise one or more pharmaceutically acceptable additional ingredient(s) such as alum, stabilizers, buffers, coloring agents, flavoring agents, and the like.

The tetracycline compound may be administered intermittently. For example, the tetracycline compound may be administered 1–6 times a day, preferably 1–4 times a day.

Alternatively, the tetracycline compound may be administered by sustained release. Sustained release administration is a method of drug delivery to achieve a certain level of the drug over a particular period of time. The level typically is measured by serum concentration. Further description of methods of delivering tetracycline compounds by sustained release can be found in the patent application, "Controlled Delivery of Tetracycline and Tetracycline Derivatives," filed on Apr. 5, 2001 and assigned to CollaGenex Pharmaceuticals, Inc. of Newtown, Pa. The aforementioned application is incorporated herein by reference in its entirety. For example, 40 milligrams of doxycycline may be administered by sustained release over a 24 hour period.

In the embodiment in which the tetracycline compound is a non-antibiotic tetracycline compound, administration can include topical application to the skin and eye. Particular non-antibiotic tetracycline compounds have only limited biodistribution, e.g. CMT-5. In such cases, topical application is the preferred method of administration of the compound.

Carrier compositions deemed to be suited for topical use include gels, salves, lotions, creams, ointments, eye drops and the like. The non-antibiotic tetracycline compound can also be incorporated with a support base or matrix or the like which can be directly applied to skin or the eye. The carrier compositions used to topically treat acne rosacea and ocular rosacea can be the same, or can be different. For example, the carrier composition used to simultaneously treat acne rosacea and ocular rosacea can both be gels. Alternatively, for example, the carrier composition used to treat acne rosacea can be an ointment, while the carrier composition used to treat ocular rosacea can be in eye drop form.

Topical application of the non-antibiotic tetracycline compounds are effective in simultaneously treating acne rosacea and ocular rosacea while not inducing significant toxicity in the human. For example, amounts of up to about 25% (w/w) in a vehicle are effective. Amounts of from about 0.1% to about 10% are preferred.

Combined or coordinated topical and systemic administration of the tetracycline compounds is also contemplated under the invention. For example, a non-absorbable non-antibiotic tetracycline compound can be administered topically, while a tetracycline compound capable of substantial absorption and effective systemic distribution in a human can be administered systemically.

The tetracycline compounds are prepared by methods known in the art. For example, natural tetracyclines may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antibiotic activity.

Further methods of preparing the tetracycline compounds are described in the examples.

EXAMPLES

The following examples serve to provide further appreciation of the invention but are not meant in any way to restrict the effective scope of the invention.

Preparation of Compounds

Example 1

4-Dedimethylamino-7-dimethylamino-6-demethyl-6-deoxy-9-nitrotetracycline sulfate To a solution of one millimole of 4-dedimethylamino-7-dimethylamino-6-demethyl-6-deoxytetracycline in 25 ml of concentrated sulfuric acid at 0° C. was added 1.05 mmole of potassium nitrate. The resulting solution was stirred at ice bath temperature for 15 minutes and poured in one liter of cold ether with stirring. The precipitated solid was allowed to settle and the majority of solvent decanted. The remaining material was filtered through a sintered glass funnel and the collected solid was washed well with cold ether. The product was dried in a vacuum desiccator overnight.

Example 2

9-amino-4-dedimethylamino-7-dimethylamino-6-demethyl-6-deoxytetracycline sulfate To a solution of 300 mg of the 9-nitro compound from example 1, in 30 ml of ethanol was added 50 mg of $PtO_2$. The mixture was hydrogenated at atmospheric pressure until the theoretical amount of hydrogen was absorbed. The system is flushed with nitrogen, the catalyst $PtO_2$ is filtered and the filtrate added dropwise to 300 ml of ether. The product that separates is filtered and dried in a vacuum desiccator.

Example 3

9-Acetamido-4-dedimethylamino-7-dimethylamino-6-demethyl-6-deoxytetracycline sulfate To a well stirred cold solution of 500 mg of 9-amino-4-dedimethylamino-7-dimethylamino-6-demethyl-6-deoxytetracycline sulfate from example 2, in 2.0 ml of 1.3-dimethyl-2-imidazolidinone, 500 mg of sodium bicarbonate was added followed by 0.21 ml of acetyl chloride. The mixture is stirred at room temperature for 30 minutes, filtered and the filtrate was added dropwise to 500 ml of ether. The product that separated was filtered and dried in a vacuum desiccator.

Example 4

4-Dedimethylamino-7-dimethylamino-6-demethyl-6-deoxy-9-diazoniumtetracycline sulfate To a solution of 0.5 g of 9-amino-4-dedimethylamino-7-dimethylamino-6-demethyl-6-deoxytetracycline sulfate, from example 2, in 10 ml of 0.1N hydrochloric acid in methanol cooled in an ice bath, 0.5 ml of n-butyl nitrite was added. The solution was stirred at ice bath temperature for 30 minutes and then poured into 250 ml of ether. The product that separated was filtered, washed with ether and dried in a vacuum desiccator.

Example 5

9-Azido-4-dedimethylamino-7-dimethylamino-6-demethyl-6-deoxytetracycline sulfate To a solution of 0.3 mmole of 4-dedimethylamino-7-dimethylamino-6-demethyl-6-deoxy-9-diazoniumtetracycline sulfate, from example 4, 10 ml of 0.1 N methanolic hydrogen chloride was added 0.33 mmole of sodium azide. The mixture was stirred at room temperature for 1.5 hours. The reaction mixture was then poured into 200 ml of ether. The product that separated was filtered and dried in a vacuum desiccator.

Example 6

9-Amino-8-chloro-4-dedimethylamino-7-dimethylamino-6-demethyl-6-deoxy-tetracycline sulfate One gram of 9-azido-4-dedimethylamino-7-dimethylamino-6-demethyl-6-deoxytetracycline hydrochloride, from example 4, was dissolved in 10 ml of concentrated sulfuric acid saturated with HCL at 0° C. The mixture was stirred at ice bath temperature for 1.5 hours and then slowly added dropwise to 500 ml of cold ether. The product that separated was filtered, washed with ether and dried in a vacuum desiccator.

Example 7

4-Dedimethylamino-7-dimethylamino-6-demethyl-6-deoxy-9-ethoxythiocarbonylthio-tetracycline sulfate A solution of 1.0 mmole of 4-dedimethylamino-7-dimethylamino-6-demethyl-6-deoxy-9-diazoniumtetracycline sulfate, from example 4, in 15 ml of water was added to a solution of 1.15 mmole of potassium ethyl xanthate in 15 ml of water. The mixture was stirred at room temperature for one hour. The product separated and was filtered and dried in a vacuum desiccator.

Example 8A

General Procedure for Nitration

To 1 mmole of a 4-dedimethylamino-6-deoxytetracycline in 25 ml of concentrated sulfuric acid at 0° C. was added 1 mmole of potassium nitrate with stirring. The reaction solution was stirred for 15 minutes and then poured into 100 g of chopped ice. The aqueous solution was extracted 5 times with 20 ml of butanol each time. The butanol extracts were washed three times with 10 ml of water each time, and concentrated in vacuo to a volume of 25 ml. The light yellow crystalline solid which precipitated was filtered, washed with 2 ml of butanol and dried in vacuo at 60° C. for 2 hours. This solid was a mixture of the two mononitro isomers.

Example 8B

4-Dedimethylamino-6-deoxy-9-nitrotetracycline

To 980 mg of the nitration product from 4-dedimethylamino-6-deoxytetracycline (a mixture of the 2 isomers) in 25 ml of methanol was added enough triethylamine to dissolve the solid. The filtered solution (pH 9.0) was adjusted to pH 5.2 with concentrated sulfuric acid. A crystalline yellow solid (236 mg.) was obtained (29% yield). The material at this point was quite pure and contained only small amounts of the 7-isomer. Final purification was accomplished by liquid partition chromatography using a diatomaceous earth packed column and the solvent system: chloroform: butanol: 0.5 M phosphate buffer (pH 2) (16:1: 10).

Example 9

4-Dedimethylamino-6-deoxy-7-nitrotetracycline

The methanol filtrate from example 8 was immediately adjusted to pH 1.0 with concentrated sulfuric acid. The light yellow crystalline solid, which was obtained as the sulfate salt. A purified free base was obtained by adjusting an aqueous solution of the sulfate salt (25 mg/ml) to pH 5.2 with 2 N sodium carbonate.

Example 10

9-Amino-4-dedimethylamino-6-deoxytetracycline

To a solution of 300 mg of the 9-nitro compound, prepared in example 8, in 30 ml of ethanol was added 50 mg of $PtO_2$. The mixture was hydrogenated at atmospheric pressure until the theoretical amount of hydrogen was absorbed. The system is flushed with nitrogen, the $PtO_2$ catalyst is filtered and the filtrate added dropwise to 300 ml of ether. The solid that separates is filtered and dried in a vacuum desiccator.

Example 11

9-Acetamido-4-dedimethylamino-6-deoxytetracycline sulfate

To well stirred cold solution of 500 mg of 9-amino-4-dedimethylamino-6-deoxytetracycline sulfate, from example 10, in 2.0 ml of 1,3-dimethyl-2-imidazolidinone was added 500 mg of sodium bicarbonate followed by 0.21 ml of acetyl chloride. The mixture was stirred at room temperature for 30 minutes, filtered and the filtrate was added dropwise to 500 ml of ether. The solid that separated was filtered and dried in a vacuum desiccator.

Example 12

4-Dedimethylamino-6-deoxy-9-diazoniumtetracycline sulfate

To a solution of 0.5 g of 9-amino-4-dedimethylamino-6-deoxytetracycline sulfate, from example 10, in 10 ml of 0.1N hydrochloric acid in methanol cooled in an ice bath was added 0.5 ml of n-butyl nitrite. The solution was stirred at ice bath temperature for 30 minutes and the poured into 250 ml of ether. The solid that separated was filtered, washed with ether and dried in a vacuum desiccator.

Example 13

9-Azido-4-dedimethylamino-6-deoxytetracycline sulfate

To a solution of 0.3 mmole of 4-dedimethylamino-6-deoxy-9-diazoniumtetracycline sulfate, of example 12, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 14

9-Amino-8-chloro-4-dedimethylamino-6-deoxytetracycline sulfate

One gram of 9-azido-4-dedimethylamino-7-dimethylamino-6-deoxytetracycline hydrochloride, from example 13, was dissolved in 10 ml of concentrated sulfuric acid saturated with HCL at 0° C. The mixture was stirred at ice bath temperature for 1.5 hours and then slowly added dropwise to 500 ml of cold ether. The solid that separated was filtered, washed and ether and dried in a vacuum desiccator.

Example 15

4-Dedimethylamino-6-deoxy-9-ethoxythiocarbonylthiotetracycline sulfate

A solution of 1.0 mmole of 4-dedimethylamino-6-deoxy-9-diazoniumtetracycline sulfate, from example 12, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 16

9-Dimethylamino-4-dedimethylamino-6-deoxytetracycline sulfate

To a solution of 100 mg. of the 9-amino compound from example 10, in 10 ml of ethylene glycol monomethyl ether is added 0.05 ml of concentrated sulfuric acid, 0.4 ml. of a 40% aqueous formaldehyde solution and 100 mg of a 10% palladium on carbon catalyst. The mixture is hydrogenated under atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried, yield, 98 mg.

Example 17

7-Amino-4-dedimethylamino-6-deoxytetracycline

This compound can be made using Procedure A or B. Procedure A. To a solution of 300 mg of the 7-nitro compound, from example 1, in 30 ml of ethanol was added 50 mg of $PtO_2$. The mixture was hydrogenated at atmospheric pressure until the theoretical amount of hydrogen was absorbed. The system is flushed with nitrogen, the catalyst $PtO_2$ is filtered and the filtrate added dropwise to 300 ml of ether. The solid that separates is filtered and dried in a vacuum desiccator.

Procedure B. 1 g of 6-deoxy-4-dedimethylamino-tetracycline was dissolved in 7.6 ml THF and 10.4 ml methanesulfonic acid at −10° C. After warming the mixture to 0° C. a solution of 0.86 g of dibenzyl azodicarboxylate was added and the mixture stirred for 2 hours at 0° C. to yield 7-[1,2-bis(carbobenzyloxy)hydrazino]-4-dedimethylamino-6-deoxytetracycline. A solution of 1 millimole of this material in 70 ml 2-methoxyethanol, and 300 mg 10% Pd-C was hydrogenated at room temperature to give 7-amino-6-deoxy-4-dedimethylaminotetracycline.

Example 18

7-Amino-6-deoxy-5-hydroxy-4-dedimethylaminotetracycline 1 g of 6-deoxy-5-hydroxy-4-dedimethylaminotetracycline 3 was dissolved in 7.6 ml THF and 10.4 ml methanesulfonic acid at −10° C. After warming the mixture to 0° C. a solution of 0.86 g dibenzyl azodicarboxylate in 0.5 ml THF was added and the mixture stirred for 2 hours at 0° C. to yield 7-[1,2-bis(carbobenzyloxy)hydrazino]-4-dedimethylamino-6-deoxy-5-hydroxytetracycline. A solution of 1 millimole of this material in 70 ml 2-methoxyethanol, and 300 mg 10% Pd-C was hydrogenated at room temperature to give 7-amino-6-deoxy-5-hydroxytetracycline.

Example 19

7-Acetamido-4-dedimethylamino-6-deoxy-5-hydroxytetracycline sulfate

To well stirred cold solution of 500 mg of 7-amino-4-dedimethylamino-6-deoxy-5-hydroxytetracycline sulfate, from example 18, in 2.0 ml of 1,3-dimethyl-2-imidazolidinone was added 500 mg of sodium bicarbonate followed by 0.21 ml of acetyl chloride. The mixture was stirred at room temperature for 30 minutes, filtered and the filtrate was added dropwise to 500 ml of ether. The solid that separated was filtered and dried in a vacuum desiccator.

Example 20

4-Dedimethylamino-6-deoxy-5-hydroxy-7-diazoniumtetracycline hydrochloride

To a solution of 0.5 g of 7-amino-4-dedimethylamino-6-deoxy-5-hydroxytetracycline sulfate, from example 20, in 10 ml of 0.1N hydrochloric acid in methanol cooled in an ice bath was added 0.5 ml of n-butyl nitrite. The solution was stirred at ice bath temperature for 30 minutes and then poured into 250 ml of ether. The solid that separated was filtered, washed with ether and dried in a vacuum desiccator.

Example 21

7-Azido-4-dedimethylamino-6-deoxy-5-hydroxytetracycline

To a solution of 0.3 mmole of 4-dedimethylamino-6-deoxy-5-hydroxy-7-diazoniumtetracycline hydrochloride, from example 20, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 22

7-Amino-8-chloro-4-dedimethylamino-6-deoxy-5-hydroxytetracycline sulfate

One gram of 7-azido-4-dedimethylamino-7-dimethylamino-6-deoxy-5-hydroxytetracycline sulfate, from example 21, was dissolved in 10 ml of concentrated sulfuric acid (previously saturated with hydrogen chloride) at 0° C. The mixture was stirred at ice bath temperature for 1.5 hours and then slowly added dropwise to 500 ml of cold ether. The solid that separated was filtered, washed with ether and dried in a vacuum desiccator.

Example 23

4-Dedimethylamino-6-deoxy-5-hydroxy-7-ethoxythiocarbonylthiotetracycline

A solution of 1.0 mmole of 4-dedimethylamino-6-deoxy-5-hydroxy-7-diazoniumtetracycline hydrochloride, from example 20, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 24

7-Dimethylamino-4-dedimethylamino-6-deoxy-5-hydroxytetracycline sulfate

To a solution of 100 mg of the 7-amino compound in 10 ml of ethylene glycol monomethyl ether is added 0.05 ml of concentrated sulfuric acid, 0.4 ml of a 40% aqueous formaldehyde solution and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried, yield, 78 mg.

Example 25

7-Diethylamino-4-dedimethylamino-5-hydroxytetracycline sulfate

To a solution of 100 mg of the 7-amino compound in 10 ml of ethylene glycol monomethyl ether is added 0.05 ml of concentrated sulfuric acid, 0.4 ml of acetaldehyde and 100 mg of a 10% palladium on carbon catalyst. The mixture is reduced with hydrogen at atmospheric pressure at room temperature for 20 minutes. The catalyst was filtered and filtrate was evaporated to dryness under reduced pressure. The residue is dissolved in 5 ml of methanol and this solution was added to 100 ml of ether. The product that separated was filtered and dried.

Example 26

4-Dedimethylamino-6-deoxy-7-diazoniumtetracycline hydrochloride

To a solution of 0.5 g. of 7-amino-4-dedimethylamino-6-deoxytetracycline sulfate, from example 17, in 10 ml of 0.1N hydrochloric acid in methanol cooled in an ice bath was added 0.5 ml of n-butyl nitrite. The solution was stirred at ice bath temperature for 30 minutes and then poured into 250 ml of ether. The solid that separated was filtered, washed with ether and dried in a vacuum desiccator.

Example 27

7-Azido-4-dedimethylamino-6-deoxytetracycline

To a solution of 0.3 mmole of 4-dedimethylamino-6-deoxy-7-diazoniumtetracycline hydrochloride, from example 26, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 28

7-Amino-8-chloro-4-dedimethylamino-6-deoxytetracycline sulfate

One gram of 7-azido-4-dedimethylamino-7-dimethylamino-6-deoxytetracycline sulfate was dissolved in 10 ml of concentrated sulfuric acid (previously saturated with hydrogen chloride) at 0° C. The mixture was stirred at ice bath temperature for 1.5 hours and then slowly added dropwise to 500 ml of cold ether. The solid that separated was filtered, washed with ether and dried in a vacuum desiccator.

Example 29

4-Dedimethylamino-6-deoxy-7-ethoxythiocarbonylthiotetracycline

A solution of 1.0 mmole of 4-dedimethylamino-6-deoxy-7-diazoniumtetracycline hydrochloride, from example 26, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 30

7-Dimethylamino-4-dedimethylamino-6-deoxytetracycline sulfate

To a solution of 100 mg of the 7-amino compound, from example 26, in 10 ml of ethylene glycol monomethyl ether is added 0.05 ml of concentrated sulfuric acid, 0.4 ml of a 40% aqueous formaldehyde solution and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried.

Example 31

9-Acetamido-8-chloro-4-dedimethylamino-7-dimethylamino-6-deoxy-6-demethyltetracycline

To well stirred cold solution of 500 mg of 9-amino-8-chloro-4-dedimethylamino-6-deoxy-6-demethyl-7-dimethyl amino tetracycline sulfate, from example 6, in 2.0 ml of 1,3-dimethyl-2-imidazolidinone was added 500 mg of sodium bicarbonate followed by 0.21 ml. of acetyl chloride. The mixture was stirred at room temperature for 30 minutes, filtered and the filtrate was added dropwise to 500 ml of ether. The solid that separated was filtered and dried in a vacuum desiccator.

Example 32

8-Chloro-4-dedimethylamino-7-dimethylamino-6-deoxy-6-demethyl-9-ethoxythiocarbonylthiotetracycline A solution of 1.0 mmole of -8-chloro-4-dedimethylamino-6-deoxy-6-demethyl-7-dimethyl amino-9-diazoniumtetracycline hydrochloride in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 33

8-Chloro-9-dimethylamino-4-dedimethylamino-7-dimethylamino-6-deoxy-6-demethytetracycline sulfate To a solution of 100 mg. of the 9-amino compound, from example 6, in 10 ml of ethylene glycol monomethyl ether is added 0.05 ml of concentrated sulfuric acid, 0.4 ml of acetaldehyde and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried.

Example 34

N-(4-methylpiperazin-1-yl) methyl-4-dedimethylamino-6-demethyl-6-deoxytetracycline An aqueous solution of 58 mg (37%) formaldehyde (0.72 mmol) was added to a solution of 203 mg (0.49 mmol) of 4-dedimethylamino-6-demethyl-6-deoxytetracycline in 5.0 ml ethylene glycol dimethyl ether. The mixture was stirred at room temperature for 0.5 hours. 56 mg (0.56 mmol) of 1-methylpiperazine was then added and the resulting mixture was stirred overnight and refluxed for 20 minutes. The mixture was then cooled and a solid product was collected by filtration. The solid product was then washed with the solvent and dried by vacuum filtration.

Example 35

N-(4-methylpiperazin-1-yl)methyl-4-dedimethylamino-6-demethyl-6-deoxy-9-hexanoylaminotetracycline An aqueous solution of 49 mg 37% formaldehyde (0.60 mmol) was added to a solution of 146 mg (0.30 mmol) of 4-dedimethylamino-6-demethyl-6-deoxy-9-hexanoylaminotetracycline in 5.0 ml ethylene glycol dimethyl ether. The mixture was stirred at room temperature for 0.5 hours. 60 mg (0.60 mmol) of 1-methylpiperazine was then added and the resulting mixture was stirred overnight and refluxed for 20 minutes. The mixture was then cooled and a solid product was collected by filtration. The solid product was then washed with the solvent and dried by vacuum filtration.

Example 36

4-Dedimethylamino-6-demethyl-6-deoxy-9-hexanoylaminotetracycline 1.54 g (7.2 mmol) of hexanoic anhydride and 150 mg of 10% Pd/C catalyst were added to 300 mg (0.72 mmol) of 4-dedimethylamino-6-demethyl-6-deoxytetracycline in 6.0 ml of 1,4-dioxane and 6.0 ml of methanol. The mixture was hydrogenated overnight at room temperature. The catalyst was removed by filtration and the filtrate was concentrated under reduced pressure. The residue was dissolved in 7 ml of ethyl acetate and triturated with 50 ml of hexane to produce a solid product. The solid product was filtered and dried by vacuum filtration.

Example 37

Phototoxicity Determination

BALB/c 3T3 (CCL-163) cells were obtained from ATCC and cultured in antibiotic-free Dulbecco's Minimum Essential Medium (4.5 g/1 glucose)(DMEM) supplemented with L-glutamine (4 mM) and 10% newborn calf serum. The working cell bank was prepared and found to be free of mycoplasma. Streptomycin sulfate (100 g/ml) and penicillin (100 IU/ml) were added to the medium after the cells were treated with test article in 96-well plates.

Serial dilutions of the tetracycline derivatives were prepared in DMSO at concentrations 100× to final testing concentration. The COL dilutions in DMSO were then diluted in Hanks' Balanced Salt Solution (HBSS) for application to the cells. The final DMSO concentration was 1% in treated and control cultures. A dose range finding assay is conducted with eight serial dilutions covering a range of 100–0.03 µg/ml in half log steps. Definitive assays are conducted with 6–8 serial dilutions prepared in quarter log steps, centered on the expected 50% toxicity point as determined in the dose range finding assay. One hundred 100 µg/ml was the highest dose recommended to prevent false negative results from UV absorption by the dosing solutions. One dose range finding and at least two definitive trials were performed on each tetracycline derivative and control compound.

Controls. Each assay included both negative (solvent) and positive controls. Twelve wells of negative control cultures were used on each 96-well plate. Chlorpromazine (Sigma Chemicals) was used as the positive control and was prepared and dosed like the test tetracycline derivatives.

Solar Simulator. A Dermalight SOL 3 solar simulator, equipped with a UVA H1 filter (320–400 nm), was adjusted to the appropriate height. Measurement of energy through the lid of a 96-well microtiter plate was carried out using a calibrated UV radiometer UVA sensor. Simulator height was adjusted to deliver 1.7±0.1 mW/cm$^2$ of UVA energy (resulting dose was 1 J/cm$^2$ per 10 minutes of exposure).

Phototoxicity Assay. Duplicate plates were prepared for each test material by seeding 10$^4$ 3T3 cells per well in complete medium 24 hours before treatment. Prior to treatment, the medium was removed, and the cells washed once with 125 µl of prewarmed HBSS. Fifty µl of prewarmed HBSS were added to each well. Fifty µl of each test article dilution were added to the appropriate wells and the plates returned to the incubator for approximately one hour. Six wells were treated with each dose of test or control article on each plate. Following the 1 hr incubation, the plates designated for the photo irradiation were exposed (with the lid on) to 1.7±0.1 mW/cm² UVA light for 50±2 minutes at room temperature resulting in an irradiation dose of 5 J/cm². Duplicate plates, designated for the measurement of cytotoxicity without light, were kept in the dark room temperature for 50±2 minutes. After the 50 minute exposure period (with or without light) the test article dilutions were decanted from the plates and the cells washed once with 125 µl of HBSS. One hundred µl of medium were added to all wells and the cells incubated as above for 24±1 hours.

After 24 hours of incubation, the medium was decanted and 100 µl of the Neutral Red containing medium were added to each well. The plates were returned to the incubator and incubated for approximately 3 hours. After 3 hours, the medium was decanted and each well rinsed once with 250 µl of HBSS. The plates were blotted to remove the HBSS and 100 µl of Neutral Red Solvent were added to each well. After a minimum of 20 minutes of incubation at room temperature (with shaking), the absorbance at 550 nm was measured with a plate reader, using the mean of the blank outer wells as the reference. Relative survival was obtained by comparing the amount of neutral red taken by each well treated with the test article and positive control to the neutral red taken up by the average of the negative wells (12 wells) on the same plate. The amount of neutral red taken up by the negative control wells is considered to be 100% survival.

There are several methods by which to quantify relative phototoxicity, e.g., the photoirritancy factor (PIF) and the mean photo effect (MPE), as discussed below.

Phototoxicity Determined by PIF Valuations

To determine the dose where there is a 50% decrease in relative viability, the relative cell viability is plotted as a function of increasing dose and a polynomial equation is calculated to produce the "best fit" line through all the points. The dose of a test substance corresponding to the point where this line crosses the 50% survival point is calculated (termed the Inhibitory Concentration 50% or $IC_{50}$) and used to compare the toxicity of the test chemical in the presence and absence of UVA/visible light.

Phototoxicity of a tetracycline derivative can be measured by its photoirritancy factor (PIF). The photo-irritancy factor (PIF) is the ratio of the $IC_{50}$ value in the absence of light to the $IC_{50}$ value in the presence of light. That is, the PIF was determined by comparing the $IC_{50}$ without UVA [$IC_{50}$(–UVA)] with the $IC_{50}$ with UVA [$IC_{50}$(+UVA)]:

$$PIF = \frac{IC_{50}(-UVA)}{IC_{50}(+UVA)}$$

$IC_{50}$ values for both the UVA exposed and non-exposed groups were determined whenever possible. If the two values are the same, the PIF is 1 and there is no phototoxic effect. If the action of the light increases toxicity, the $IC_{50}$ with light will be lower than the $IC_{50}$ without light, and the PIF will increase.

If $IC_{50}$(+UVA) can be determined but $IC_{50}$(–UVA) cannot, the PIF cannot be calculated, although the compound tested may have some level of phototoxic potential. In this case, a ">PIF" can be calculated and the highest testable dose (–UVA) will be used for calculation of the ">PIF."

$$> PIF = \frac{\text{maximum dose } (-UVA)}{IC_{50}(+UVA)}$$

If both, $IC_{50}$(–UVA) and $IC_{50}$(+UVA) cannot be calculated because the chemical does not show cytotoxicty (50% reduction in viability) up to the highest dose tested, this would indicate a lack of phototoxic potential.

In calculating PIF values, the data resulting from the assay procedure can be interpreted by different methods.

For example, during the period Mar. 2, 1999 to Apr. 16, 1999, PIF values were obtained using the earlier phototoxicity software and its curve-fitting algorithms, i.e. PIF1.

Since April 1999, the 3T3 phototoxicity assay has undergone extensive validation, and has now been incorporated into a draft guideline by the Organization of Economic Cooperation and Development (OECD) (Draft Guideline 432). (See Spielmann et al., The International EU/COLIPA *In Vitro* Phototoxicity Validation Study; Results of Phase II (blind trial). Part 1: The 3T3 NRU Phototoxicity Test. Toxicology *In Vitro* 12:305–327 (1998); and Spielmann et al., A Study on UV Filter Chemicals from Annex VII of European Union Directive 76/768/EEC, in the *In Vitro* 3T3 Phototoxicity Test. ATLA 26:679–708 (1998).) The new guideline follows the same assay procedure, but provides some additional guidance in the interpretation of the resulting data, and incorporates updated software. As used herein, the PIF value interpreted by this method is termed PIF2.

According to this updated OECD draft guideline, the $IC_{50}$ values are developed from curves fitted to the data by a multiple boot strap algorithm. The curve fitting and calculations of the PIF are performed by software developed under contract to the German government (ZEBET, Berlin).

In particular, since there are six wells (and therefore six relative survival values) for each dose, the software performs multiple calculations of the best fit line using what is called boot strapping. This approach is used to account for variations in the data. From the bootstrapped curves, the software determines a mean $IC_{50}$ for the treatment. The $IC_{50}$ is used to compare the toxicity of the test chemical in the presence and absence of UVA/visible light. FIG. 2 shows an example of a set of dose response curves prepared for the positive control chemical Chlorpromazine. The difference in the $IC_{50}$ values can be clearly seen in this example of a highly phototoxic chemical.

Using the original software and evaluation procedures, if both $IC_{50}$ values can be determined, the cut off value of the factor to discriminate between phototoxicants and non-phototoxicants is a factor of 5. A factor greater than 5 is indicative of phototoxic potential of the test material. Using this software, the mean PIF 1 for COL 10 was determined to be 1.83. The mean PIF1 for COL 1002 was determined to be 1.12.

The OECD draft guideline has revised the values for the PIF used to differentiate between phototoxins, potential phototoxins and non-phototoxins. A PIF2 of less than 2 is considered non-phototoxic, 2 to less than 5 is considered potentially phototoxic, and 5 or greater is considered clearly phototoxic. In accordance with the OECD draft guideline, the mean PIF2 values of COL 10 and COL 1002 are 2.04 and 1.35, respectively.

Phototoxicity Determined by MPE Valuations

At each data point, a photo effect is calculated according to the following formula:

Photo Effect$_c$=Dose Effect$_c$×Response Effect$_c$ (i.e., $PE_c = DE_c \times RE_c$)

where c represents one concentration

Dose Effect$_c$ compares the dose required to achieve percent survival n without UVA (c) with the dose required to achieve the same percent survival with UVA (c'):

$$\text{Dose Effect}_n = \frac{\left|\dfrac{\text{Dose }(-UVA)\text{ to give survival }n}{\text{Dose }(+UVA)\text{ to give survival }n} - 1\right|}{\dfrac{\text{Dose }(-UVA)\text{ to give survival }n}{\text{Dose }(+UVA)\text{ to give survival }n} + 1}$$

As the ratio increases, the Dose Effect term approaches 1.

In the example in FIG. 3, the Dose Effect is calculated for one point. The dose of 0.4 dose units is required to reduce cell viability (termed response on the y axis) to 66% in the absence of light while only 0.16 dose units are required to similarly reduce viability in the presence of light. The dose effect for 0.4 dose units is:

$$DE_{0.4} = \frac{|(0.4/0.16) - 1|}{|(0.4/0.16) + 1|} = 0.43$$

The Response Effect at dose c compares the percent survival with and without UVA at that dose and normalizes for the total range of the response over the range of doses evaluated ($n_1$ to $n_i$).

$$\text{Response Effect}_c = \frac{R(-UVA)c - R(+UVA)c}{R_0}$$

where $R_0$ is the Total Survival Range (up to 100%), $R(-UVA)c$ is the survival without UVA at dose c, and $R(+UVA)c$ is the survival with UVA at dose c.

As the difference between the survival without UVA at dose c and the survival with UVA at dose c [ie., R(−UVA) c−R(+UVA)c] increases (indicative of phototoxic potential), then the Response Effect$_c$ approaches 1.0.

Again in FIG. 3, the Response Effect for the 0.4 dose is:

$RE_{0.4}=(66\%-11\%)/100\%=0.55$

The PE in this example is $PE_{0.4}=0.43*0.55=0.24$

The Mean Photo Effect is the mean of the individual Photo Effect values over the range evaluated. It is produced from the formula:

$$MPE = \frac{\sum_{i=1}^{n} w_i * PE_{ci}}{\sum_{i=1}^{n} w_i}$$

where $w_i$ is a weighting factor for the highest viability observed for each curve.

The MPE value is used to determine phototoxic potential. In the original analysis of the validation data, a material was considered nonphototoxic if the MPE was <0.1 (this includes negative MPE values) and phototoxic if the MPE was ≧0.1 (Spielmann et al, 1998). This cut off was re-examined once the software had been rewritten and the weighting factor added. In the draft Organization for Economic Cooperation and Development phototoxicity test guideline (Guideline 432), MPE values of <0.1 (including negative values) are considered indicative of a nonphototoxin, values of 0.1 to <0.15 are considered probable phototoxins, and greater than and equal to 0.15 clear phototoxins. This guideline is expected to become the standard after final approval in 2003. The software used to calculate the MPE values is part of this guideline.

The following table shows the phototoxicity values for several tetracycline derivatives. The positive control is chlorpromazine. The phototoxicity is evaluated in terms of MPE and in terms of PIF using the new OECD draft guideline.

| PHOTOTOXICITY VALUES | | | |
|---|---|---|---|
| COMPOUND | MPE | PIF 1 | PIF 2 |
| Chlorpromazine | 0.639 | N/D | 40.38 |
| Tetracycline | 0.340 | 5.38 | N/A |
| Doxycycline | 0.522 | 23.37 | 26.71 |
| Minocycline | 0.041 | 2.04 | N/A |
| COL 10 | 0.099 | 1.82 | 2.04 |
| COL 1 | 0.460 | N/D | N/A |
| COL 2 | 0.005 | N/D | N/A |
| COL 3 | 0.654 | 647 | 84.72 |
| COL 302 | 0.378 | 23.16 | 23.32 |
| COL 303 | 0.309 | 5.27 | 13.82 |
| COL 305 | 0.420 | N/D | N/A |
| COL 306 | 0.038 | 1.64 | 1.56 |
| COL 307 | 0.056 | 1.17 | N/A |
| COL 308 | 0.015 | 1.0 | N/A |
| COL 309 | 0.170 | 5.17 | 12.87 |
| COL 311 | 0.013 | 1.0 | N/A |
| COL 312 | 0.442 | 62.67 | 75.11 |
| COL 313 | 0.462 | 80.27 | 58.22 |
| COL 314 | 0.475 | 41.1 | 89.48 |
| COL 315 | 0.276 | 15.8 | 35.30 |
| COL 4 | 0.570 | N/D | N/A |
| COL 5 | 0.186 | N/D | N/A |
| COL 6 | 0.155 | N/D | N/A |
| COL 7 | 0.531 | N/D | N/A |
| COL 8 | 0.703 | 165 | 82.61 |
| COL 801 | −0.001 | 1.0 | N/A |
| COL 802 | −0.123 | 1.0 | N/A |
| COL 803 | 0.047 | N/D | N/A |
| COL 804 | 0.003 | 1.0 | N/A |
| COL 805 | 0.022 | 1.0 | N/A |
| COL 807 | 0.382 | 40.4 | N/A |
| COL 808 | 0.387 | 46.45 | N/A |
| COL 809 | 0.420 | N/D | N/A |
| COL 9 | 0.546 | N/D | N/A |
| COL 1001 | 0.025 | N/D | N/A |
| COL 1002 | 0.040 | 1.0 | 1.35 |

N/A indicates that the $IC_{50}$ value could not be determined for the UVA exposed and/or non-exposed groups
N/D indicates that the PIF1 was not determined for the particular compound, or was N/A as defined above.

In the present specification, some of the compounds of the invention are referred to by codes names. The correspondence between the compound and codes names are as follows:

| CHEMICAL NAMES OF THE COL COMPOUNDS | |
|---|---|
| COL-1 | 4-dedimethylaminotetracycline |
| COL-3 | 6-demethyl-6-deoxy-4-dedimethylaminotetracycline |
| COL-301 | 7-bromo-6-demethyl-6-deoxy-4-dedimethylaminotetracycline |
| COL-302 | 7-nitro-6-demethyl-6-deoxy-4-dedimethylaminotetracycline |
| COL-303 | 9-nitro-6-demethyl-6-deoxy-4-dedimethylaminotetracycline |
| COL-304 | 7-acetamido-6-demethyl-6-deoxy-4-dedimethylaminotetracycline |
| COL-305 | 9-acetamido-6-demethyl-6-deoxy-4-dedimethylaminotetracycline |
| COL-306 | 9-dimethylamino-6-demethyl-6-deoxy-4-dedimethylaminotetracycline |
| COL-307 | 7-amino-6-demethyl-6-deoxy-4-dedimethylaminotetracycline |
| COL-308 | 9-amino-6-demethyl-6-deoxy-4-dedimethylaminotetracycline |
| COL-309 | 9-dimethylaminoacetamido-6-demethyl-6-deoxy-4-dedimethylaminotetracycline |
| COL-310 | 7-dimethylamino-6-demethyl-6-deoxy-4-dedimethylaminotetracycline |
| COL-311 | 9-palmitamide-6-demethyl-6-deoxy-4-dedimethylaminotetracycline |
| COL-312 | 2-CONHCH$_2$-pyrrolidin-1-yl-6-demethyl-6-deoxy-4-dedimethylaminotetracycline |
| COL-313 | 2-CONHCH$_2$-piperidin-1-yl-6-demethyl-6-deoxy-4-dedimethylaminotetracycline |
| COL-314 | 2-CONHCH$_2$-morpholin-1-yl-6-demethyl-6-deoxy-4-dedimethylaminotetracycline |
| COL-315 | 2-CONHCH$_2$-piperazin-1-yl-6-demethyl-6-deoxy-4-dedimethylaminotetracycline |
| COL-4 | 7-chloro-4-dedimethylaminotetracycline |
| COL-5 | tetracycline pyrazole |
| COL-6 | 4-hydroxy-4-dedimethylaminotetracycline |
| COL-7 | 4-dedimethylamino-12α-deoxytetracycline |
| COL-8 | 4-dedimethylaminodoxycycline |
| COL-801 | 9-acetamido-4-dedimethylaminodoxycycline |
| COL-802 | 9-dimethylaminoacetamido-4-dedimethylaminodoxycycline |
| COL-803 | 9-palmitamide-4-dedimethylaminodoxycycline |
| COL-804 | 9-nitro-4-dedimethylaminodoxycycline |
| COL-805 | 9-amino-4-dedimethylaminodoxycycline |
| COL-806 | 9-dimethylamino-4-dedimethylaminodoxycycline |
| COL-807 | 2-CONHCH$_2$-pyrrolidin-1-yl-4-dedimethylaminodoxycycline |
| COL-808 | 2-CONHCH$_2$-piperidin-1-yl-4-dedimethylaminodoxycycline |
| COL-809 | 2-CONHCH$_2$-piperazin-1-yl-4-dedimethylaminodoxycycline |
| COL-10 | 4-dedimethylaminominocycline (a.k.a. COL-310) |
| COL-1001 | 7-trimethylammonium-4-dedimethylaminosancycline |
| COL-1002 | 9-nitro-4-dedimethylaminominocycline |

Index of Structures

Structure C

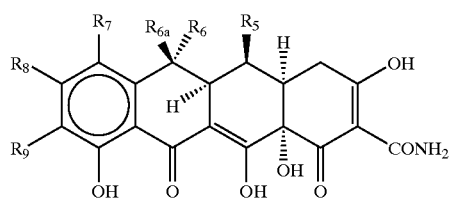

Structure D

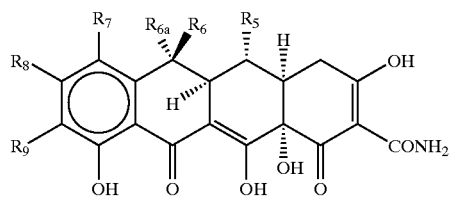

Structure E

Structure F

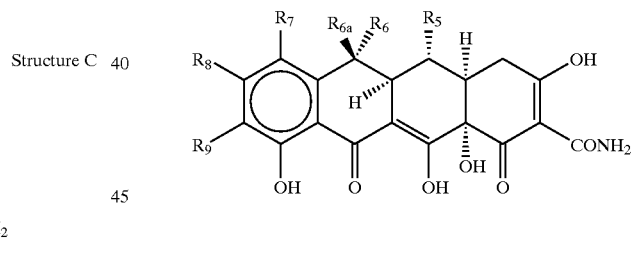

wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and RCH(NH$_2$)CO; R is hydrogen or lower alkyl; and pharmaceutically acceptable and unacceptable salts thereof; with the following provisos: when either R7 and R9 are hydrogen then R8 must be halogen; and when R6-a, R6, R5 and R9 are all hydrogen and R7 is hydrogen, amino, nitro, halogen, dimethylamino or diethylamino, then R8 must be halogen; and when R6-a is methyl, R6 and R9 are both hydrogen, R5 is hydroxyl and R7 is hydrogen, amino, nitro, halogen or diethylamino, then R8 is halogen; and when R6-a is methyl, R6 is hydroxyl, R5, R7 and R9 are all hydrogen, then R8 must be halogen; and when R6-a, R6 and R5 are all hydrogen, R9 is methylamino and R7 is dimethylamino, then R8 must be halogen; and when R6-a is methyl, R6 is hydrogen, R5 is hydroxyl, R9 is methylamino and R7 is dimethylamino, then R8 must be halogen; and when R6-a is methyl, R6, R5 and R9 are all hydrogen and R7 is cyano, then R8 must be halogen.

Structure G

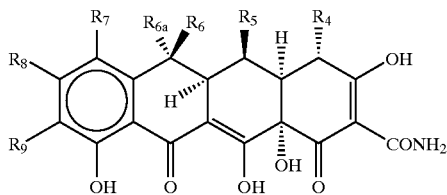

Structure H

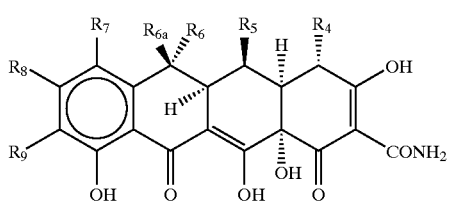

Structure I

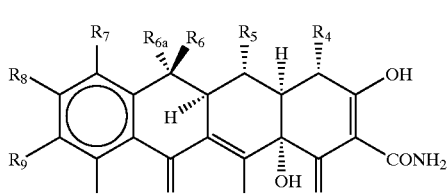

Structure J

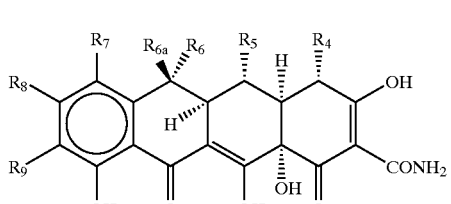

wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R4 is selected from the group consisting of NOH, N-NH-A, and NH—A, where A is a lower alkyl group; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; R is hydrogen or lower alkyl; and pharmaceutically acceptable and unacceptable salts thereof; with the following provisos: when R4 is NOH, N—NH-alkyl or NH-alkyl and R7, R6-a, R6, R5, and R9 are all hydrogen, then R8 must be halogen; and when R4 is NOH, R6-a is methyl, R6 is hydrogen or hydroxyl, R7 is halogen, R5 and R9 are both hydrogen, then R8 must be halogen; and when R4 is N—NH-alkyl, R6-a is methyl, R6 is hydroxyl and R7, R5, R9 are all hydrogen, then R8 must be halogen; and when R4 is NH-alkyl, R6-a, R6, R5 and R9 are all hydrogen, R7 is hydrogen, amino, mono(lower alkyl)amino, halogen, di(lower alkyl)amino or hydroxyl, then R8 must be halogen; and when R4 is NH-alkyl, R6-a is methyl, R6 and R9 are both hydrogen, R5 is hydroxyl, and R7 is mono(lower alkyl)amino or di(lower alkyl)amino, then R8 must be halogen; and when R4 is NH-alkyl, R6-a is methyl, R6 is hydroxy or hydrogen and R7, R5, and R9 are all be hydrogen, then R8 must be halogen.

General Formula (I)

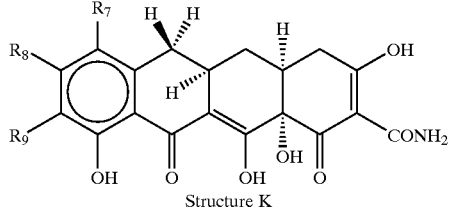

Structure K wherein R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| dimethylamino | hydrogen | diazonium |
| dimethylamino | chloro | amino |
| hydrogen | chloro | amino |
| amino | chloro | amino |
| acylamino | chloro | acylamino |
| amino | chloro | hydrogen |
| acylamino | chloro | hydrogen |
| monoalkylamino | chloro | amino |
| nitro | chloro | amino |
| dimethylamino | chloro | acylamino |
| dimethylamino | chloro | dimethylamino |
| dimethylamino | hydrogen | hydrogen |
| hydrogen | hydrogen | dimethylamino |
| trimethylammonium | hydrogen | hydrogen | and

General Formula (II)

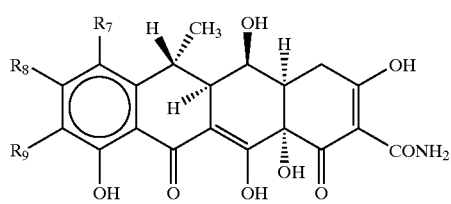

Structure L

| R7 | R8 | R9 |
|----|----|----|

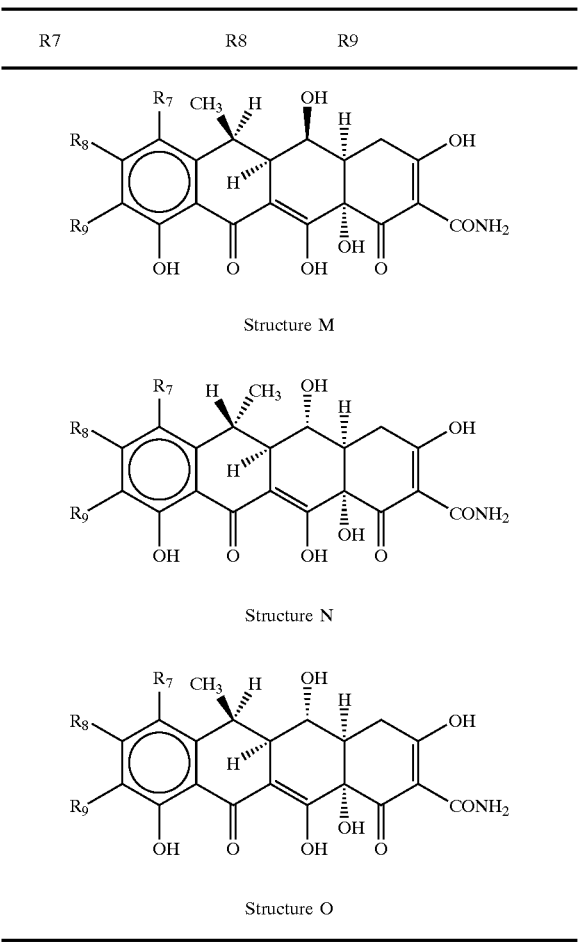

Structure M

Structure N

Structure O wherein R7, R8, and R9 taken together in each case, have the following meanings:

| R7 | R8 | R9 |
|----|----|----|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| hydrogen | hydrogen | diazonium |
| hydrogen | hydrogen | dimethylamino |
| diazonium | hydrogen | hydrogen |
| ethoxythiocarbonylthio | hydrogen | hydrogen |
| dimethylamino | chloro | amino |
| amino | chloro | amino |
| acylamino | chloro | acylamino |
| hydrogen | chloro | amino |
| amino | chloro | hydrogen |
| acylamino | chloro | hydrogen |
| monoalkyl amino | chloro | amino |
| nitro | chloro | amino |

| R7 | R8 | R9 |
|----|----|----| and

General Formula (III)

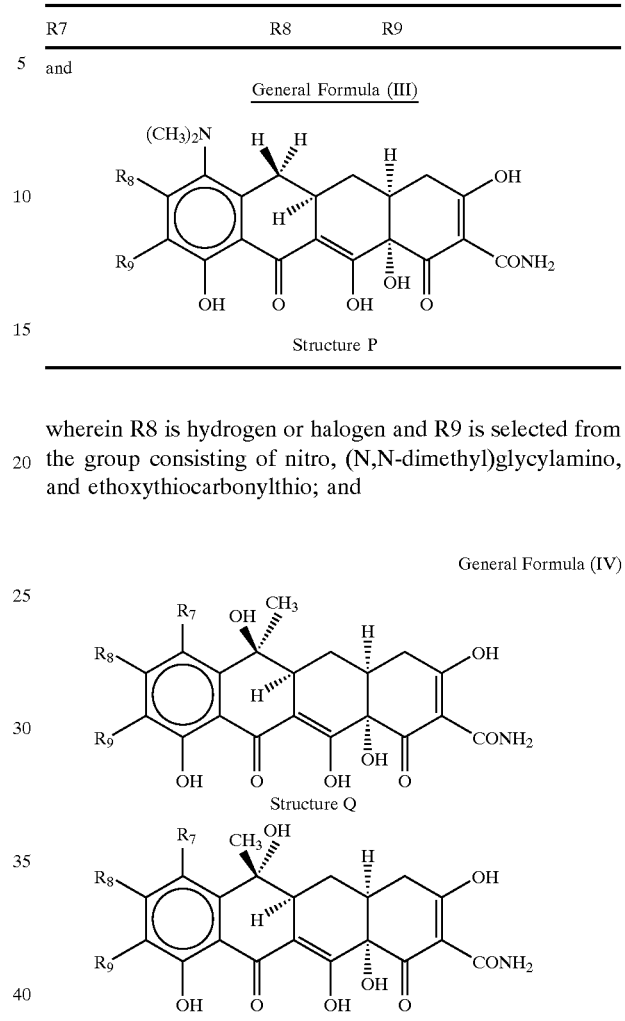

Structure P wherein R8 is hydrogen or halogen and R9 is selected from the group consisting of nitro, (N,N-dimethyl)glycylamino, and ethoxythiocarbonylthio; and General Formula (IV)

Structure Q

Structure R wherein R7, R8, and R9 taken together in each case, have the following meanings:

| R7 | R8 | R9 |
|----|----|----|
| amino | hydrogen | hydrogen |
| nitro | hydrogen | hydrogen |
| azido | hydrogen | hydrogen |
| dimethylamino | hydrogen | azido |
| hydrogen | hydrogen | amino |
| hydrogen | hydrogen | azido |
| hydrogen | hydrogen | nitro |
| bromo | hydrogen | hydrogen |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| diethylamino | hydrogen | hydrogen |
| hydrogen | hydrogen | ethoxythiocarbonylthio |
| dimethylamino | hydrogen | methylamino |
| dimethylamino | hydrogen | acylamino |
| dimethylamino | chloro | amino |
| amino | chloro | amino |

| R7 | R8 | R9 |
|---|---|---|
| acylamino | chloro | acylamino |
| hydrogen | chloro | amino |
| amino | chloro | hydrogen |
| acylamino | chloro | hydrogen |
| monoalkylamino | chloro | amino |
| nitro | chloro | amino | and pharmaceutically acceptable and unacceptable salts thereof.

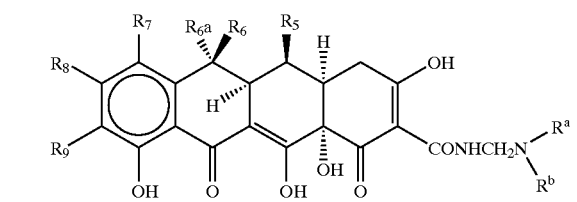

Structure S

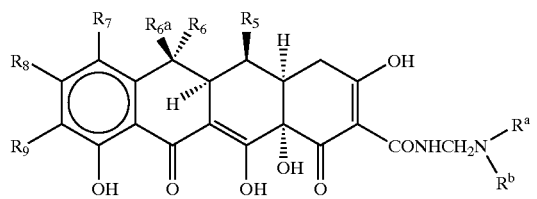

Structure T

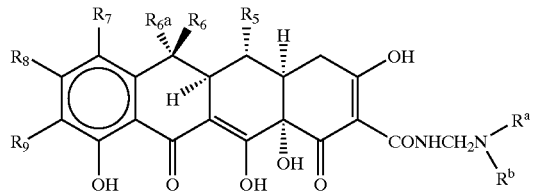

Structure U

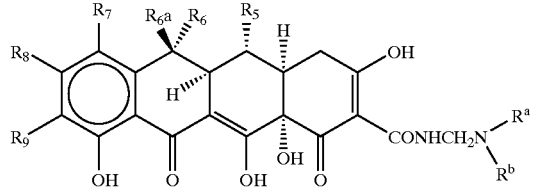

Structure V

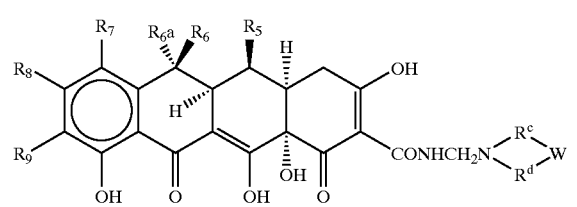

Structure W

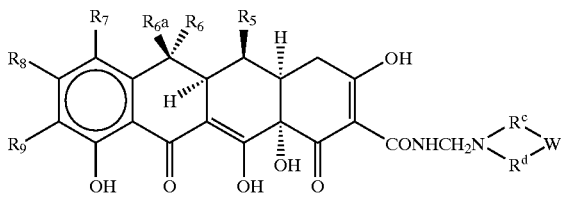

Structure X

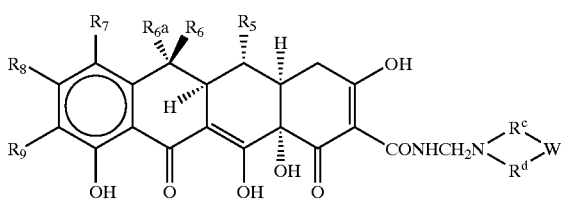

Structure Y

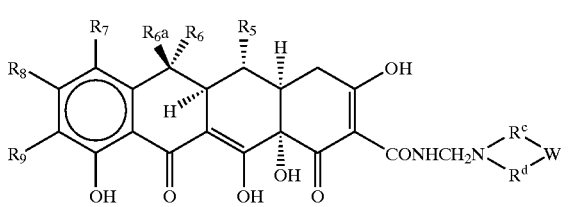

Structure Z

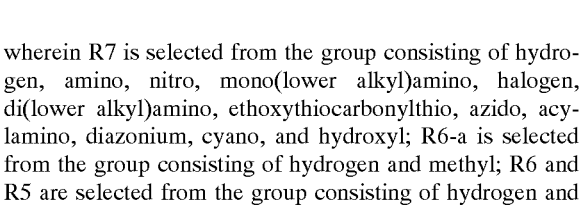

wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and $RCH(NH_2)CO$; R is hydrogen or lower alkyl; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and, W is selected from the group consisting of $(CHR^e)_m$ wherein m is 0–3 and $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof. In a further embodiment, the following provisos apply: when either R7 and R9 are hydrogen then R8 must be halogen; and when R6-a, R6, R5 and R9 are all hydrogen and R7 is hydrogen, amino, nitro, halogen, dimethylamino or diethylamino, then R8 must be halogen; and when R6-a is methyl, R6 and R9 are both hydrogen, R5 is hydroxyl, and R7 is hydrogen, amino, nitro, halogen or diethylamino, then R8 is halogen; and when R6-a is methyl, R6 is hydroxyl, R5, R7 and R9 are all hydrogen, then R8 must be halogen; and when R6-a, R6 and R5 are all hydrogen, R9 is methylamino and R7 is dimethylamino, then R8 must be halogen; and when R6-a is methyl, R6 is hydrogen, R5 is hydroxyl, R9 is methylamino and R7 is dimethylamino, then R8 must be halogen; and when R6-a is methyl, R6, R5 and R9 are all hydrogen and R7 is cyano, then R8 must be halogen.

Structure K wherein: R7, R8, and R9 taken together in each case, have the following meanings:

| R7 | R8 | R9 |
|---|---|---|
| hydrogen | hydrogen | amino |
| hydrogen | hydrogen and | palmitamide |
| STRUCTURE L | STRUCTURE M | STRUCTURE N | STRUCTURE O | wherein: R7, R8, and R9 taken together in each case, have the following meanings:

| R7 | R8 | R9 |
|---|---|---|
| hydrogen | hydrogen | acetamido |
| hydrogen | hydrogen | dimethylaminoacetamido |
| hydrogen | hydrogen | nitro |
| hydrogen | hydrogen and STRUCTURE P | amino | wherein: R8, and R9 taken together are, respectively, hydrogen and nitro.

Structure K wherein: R7, R8, and R9 taken together are, respectively, hydrogen, hydrogen and dimethylamino.

Structure C Structure D Structure E Sturcture F wherein R7 is selected from the group consisting of an aryl, alkenyl and alkynyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and RCH(NH$_2$)CO; and pharmaceutically acceptable and unacceptable salts thereof;
or Structure C Structure D Structure E Structure F wherein: R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of an aryl, alkenyl and alkynyl; and pharmaceutically acceptable and unacceptable salts thereof;
or Structure C Structure D Structure E Structure F wherein: R7 and R9 are selected from the group consisting of an aryl, alkene, alkyne, or mixures thereof; R6-a is selected from the group consisting of hydrogen and methyl; R6 and R5 are selected from the group consisting of hydrogen and hydroxyl; R8 is selected from the group consisting of hydrogen and halogen; and pharmaceutically acceptable and unacceptable salts thereof.

Structure G Sturcture H Structrue I Structure J wherein R7 is selected from the group consisting of an aryl, alkenyl and alkynyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen;R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; and pharmaceutically acceptable and unacceptable salts thereof;
or Structure G Structure H Structure I Structure J wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of an aryl, alkenyl and alkynyl; and pharmaceutically acceptable and unacceptable salts thereof;
or Structure G Structure H Structure I Structure J wherein: R7 and R9 are selected from the group consisting of an aryl, alkenyl, alkynyl; or mixtures thereof; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; and R8 is selected from the group consisting of hydrogen and halogen; and pharmaceutically acceptable and unacceptable salts thereof.

Structure K wherein R7 is selected from the group consisting of an aryl, alkenyl and alkynyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; and pharmaceutically acceptable and unacceptable salts thereof;
or

Structure K wherein: R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof;

or

Structure K wherein: R7 and R9 are selected from the group consisting of an aryl, alkenyl, alkynyl and mixtures thereof; and R8 is selected from the group consisting of hydrogen and halogen; and pharmaceutically acceptable and unacceptable salts thereof;

and

Structure L Structure M Structure N Structure O wherein: R7 is selected from the group consisting of an aryl, alkenyl and alkynyl; R8 is selected from the group consisting of hydrogen and halogen; and pharmaceutically acceptable and unacceptable salts thereof;

or

Structure L Structure M Structure N Structure O wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof;

or

Structure L Structure M Structure N Structure O wherein R7 is and R9 are selected from the group consisting of an aryl, alkenyl, alkynyl and mixtures thereof; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl) amino and $RCH(NH_2)CO$; and pharmaceutically acceptable and unacceptable salts thereof;

and

Structure P wherein R9 is selected from the group consisting of an aryl, alkenyl and alkynyl; and R8 is selected from the group consisting of hydrogen and halogen; and pharmaceutically acceptable and unacceptable salts thereof;

and

Structure Q Structure R wherein R7 is selected from the group consisting of an aryl, alkenyl and alkynyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and $RCH(NH_2)CO$; and pharmaceutically acceptable and unacceptable salts thereof;

or

Structure Q Structure R wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof;

or

Structure Q Structure R wherein R7 and R9 are selected from the group consisting of an aryl, alkenyl, alkynyl; and mixtures thereof; R8 is selected from the group consisting of hydrogen and halogen; and pharmaceutically acceptable and unacceptable salts thereof.

Structures S–Z wherein R7 is selected from the group consisting of an aryl, alkenyl and alkynyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and $RCH(NH_2)CO$; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and,W is selected from the group consisting of $(CHR^e)_m$ wherein m is 0–3 and said $R^e$ is as above, NH, $N(C_1$–$C_3)$ straight chained or branched alkyl, O, S and $N(C_1$–$C_4)$ straight chain or branched alkoxy; and pharmaceutically acceptable and unacceptable salts thereof;

or

Structures S–Z wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of an aryl, alkenyl and alkynyl; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and, W is selected from the group consisting of $(CHR^e)_m$ wherein m is 0–3 and said $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof;

or

Structures S–Z wherein: R7 and R9 are selected from the group consisting of an aryl, alkenyl, alkynyl and mixtures thereof; R6-a is selected from the group consisting of hydrogen and methyl; R6 and R5 are selected from the group consisting of hydrogen and hydroxyl; R8 is selected from the group consisting of hydrogen and halogen; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_n CHR^e$ wherein n is 0 or 1 and $R^e$ is selected from the group consisting of hydrogen, alkyl, hydroxy, lower($C_1$–$C_3$) alkoxy, amino, or nitro; and W is selected from the group consisting of $(CHR^e)_m$ wherein m is 0–3 and said $R^e$ is as above, NH, N($C_1$–$C_3$) straight chained or branched alkyl, O, S and N($C_1$–$C_4$) straight chain or branched alkoxy; and pharmaceutically acceptable and unacceptable salts thereof.

Throughout this specification, the descriptions of some structures include the term "lower alkyl." The term "lower alkyl" means an alkyl group comprising relatively few carbon atoms, for example, about one to ten carbon atoms. A preferred low end of this range is one, two, three, four or five carbon atoms; and a preferred high end of this range is six, seven, eight, nine or ten carbon atoms. Some examples of "lower alkyl" groups include methyl groups, ethyl groups, propyl groups, isopropyl groups, butyl groups, etc.

What is claimed is:

1. A method for simultaneously treating ocular rasacea and acne rosacea in a human in need thereof, the method comprising orally or intravenously administering a sub-antimicrobial amount of doxycycline to the human twice a day in a dose of 20 mg, wherein doxycycline is the single agent effective to treat ocular rosacea and acne rosacea.

2. A method for simultaneously treating ocular rosacea and acne rosacea in a human in need thereof, the method comprising orally or intravenously administering a sub-antimicrobial amount of doxycycline in an amount of 20 milligrams once daily to the human, wherein doxycycline is the single agent effective to treat ocular rosacea and acne rosacea.

3. A method for simultaneously treating ocular rosacea and acne rosacea in a human in need thereof, the method comprising orally or intravenously administering a sub-antimicrobial amount of doxycycline in an amount of 40 milligrams to the human by sustained release over a 24 hour period, wherein doxycycline is the single agent effective to treat ocular rosacea and acne rosacea.

* * * * *

UNITED STATES PATENT AND TRADEMARK OFFICE
CERTIFICATE OF CORRECTION

PATENT NO. : 7,008,631 B2  Page 1 of 1
APPLICATION NO. : 10/414808
DATED : March 7, 2006
INVENTOR(S) : Ashley It is certified that error appears in the above-identified patent and that said Letters Patent is hereby corrected as shown below:

IN THE CLAIMS:

Column 36, claim 1, line 12    Now reads:    "ocular rasacea"

Should read:    --ocular rosacea--

Signed and Sealed this

Twelfth Day of June, 2007

JON W. DUDAS
*Director of the United States Patent and Trademark Office*